US010022199B2

(12) United States Patent
Gassner et al.

(10) Patent No.: US 10,022,199 B2
(45) Date of Patent: Jul. 17, 2018

(54) REGISTRATION CORRECTION BASED ON SHIFT DETECTION IN IMAGE DATA

(71) Applicant: Brainlab AG, Munich (DE)

(72) Inventors: Jürgen Gassner, Unterfoehring (DE); Uli Mezger, Heimstetten (DE); Valentin Elefteriu, Kirchheim (DE); Swen Woerlein, Munich (DE)

(73) Assignee: Brainlab AG, Munich (DE)

( * ) Notice: Subject to any disclaimer, the term of this patent is extended or adjusted under 35 U.S.C. 154(b) by 295 days.

(21) Appl. No.: 14/762,904

(22) PCT Filed: Jan. 29, 2013

(86) PCT No.: PCT/EP2013/051640
§ 371 (c)(1),
(2) Date: Jul. 23, 2015

(87) PCT Pub. No.: WO2014/117806
PCT Pub. Date: Aug. 7, 2014

(65) Prior Publication Data
US 2015/0320512 A1 Nov. 12, 2015

(51) Int. Cl.
*A61B 90/20* (2016.01)
*A61B 34/00* (2016.01)
(Continued)

(52) U.S. Cl.
CPC .............. *A61B 90/20* (2016.02); *A61B 34/25* (2016.02); *A61B 90/37* (2016.02);
(Continued)

(58) Field of Classification Search
CPC ......... A61B 90/20; A61B 90/37; A61B 34/25; A61B 2034/2055; A61B 2090/364; A61B 2090/367; A61B 2090/373
(Continued)

(56) References Cited

U.S. PATENT DOCUMENTS

2002/0188194 A1* 12/2002 Cosman ................ A61B 5/742
600/411
2008/0119712 A1 5/2008 Lloyd
(Continued)

OTHER PUBLICATIONS

European Patent Office, International Search Report of PCT/EP2013/051640 dated Oct. 14, 2013, pp. 1-3, European Patent Office, Rijswijk, Netherlands.

*Primary Examiner* — William C Vaughn, Jr.
*Assistant Examiner* — Jae N Noh
(74) *Attorney, Agent, or Firm* — Middleton Reutlinger

(57) ABSTRACT

The invention relates to a data processing method of determining a positional transformation (T, M) for correcting the registration of an anatomical body part with a medical imaging apparatus, the method being executed by a computer and comprising the following steps: a) acquiring initial body part position data comprising initial body part position information describing an initial relative position (1) between the medical imaging apparatus and the anatomical body part; b) acquiring, from the medical imaging apparatus, body part medical image data comprising body part medical image information describing an image of the anatomical body part; c) acquiring, based on the body part medical imaging data, actual body part position data comprising actual body part position information describing an actual relative position (2, 4) between the anatomical body part and the medical imaging apparatus; d) determining, based on the actual body part position data and the initial body part position data, body part position transformation data comprising body part position transformation information describing a transformation (T, M) between the initial relative position (1) between the anatomical body part and the medical imaging apparatus, and the actual relative position (2, 4) between the anatomical body part and the medical imaging apparatus.

12 Claims, 7 Drawing Sheets

(51) Int. Cl.
*A61B 90/00* (2016.01)
*A61B 34/20* (2016.01)

(52) U.S. Cl.
CPC . *A61B 2034/2055* (2016.02); *A61B 2090/364* (2016.02); *A61B 2090/367* (2016.02); *A61B 2090/373* (2016.02)

(58) Field of Classification Search
USPC .......................................................... 348/79
See application file for complete search history.

(56) References Cited

U.S. PATENT DOCUMENTS

2008/0300477 A1   12/2008  Lloyd
2013/0070142 A1*   3/2013  Okazawa ........... H04N 5/23212
                                              348/333.01

\* cited by examiner

REGISTRATION CORRECTION BASED ON SHIFT DETECTION IN IMAGE DATA

The present invention is directed to a method, in particular data processing method, of determining a positional transformation for registering, in particular correcting the registration of, an anatomical body part with a medical imaging apparatus in accordance with claim 1, a corresponding computer program, program storage medium storing that program, computer running the program and a navigation system comprising that computer.

In navigated medical procedures, in particular image-guided surgery, it is desirable to have precise knowledge of a spatial relationship between an imaging apparatus which is used to image an anatomical body part and the anatomical body part itself. To this end, the positions of the imaging apparatus and the anatomical body part are preferably described in a common coordinate system which is used as a reference frame for navigation. Such a spatial relationship is in general established at the beginning of the medical procedure but may be flawed in particular in cases in which the navigation reference system is centered in the patient, i.e. rests relative to the patient, and the patient unexpectedly moves in a global reference system (in particular relative to the imaging apparatus). In that case, the whole navigation reference system is moved and the position of emitting apparatus is then normally no longer well-defined in the navigation reference system.

Current methods of providing an online determination of the spatial relationship between the imaging apparatus and the anatomical body part at any stage of the medical procedure involve determining their positions based on tracking markers having a predetermined and preferably fixed spatial relationship relative to the imaging apparatus and the anatomical body part, respectively. In particular, such markers are attached to each of the imaging apparatus and the anatomical body part. Such approaches, however, bring along a comparatively high demand for hardware and may be subject to errors due to for example contamination of the markers and/or a detection device used for detecting their positions. Furthermore, the spatial relationship between the markers and each of the imaging apparatus and the anatomical body part is associated with unavoidable measurement errors, and the markers may disappear from the field of view of the detection device at certain stages of the medical procedure.

The present invention therefore seeks to solve the problem of providing a method of correcting the registration of an anatomical body part with a medical imaging apparatus which is efficient and reliable and in particular allows for an update of the registration in case the patient is moved.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

Preferably, the invention provides a data processing method of determining a positional transformation for correcting the registration of an anatomical body part with a medical imaging apparatus. As said above, the spatial relationship, in particular the position and/or orientation, between the anatomical body part and the medical imaging apparatus is desirably known in order to be able to determine information about the position of the anatomical body part (which is imaged by the medical imaging apparatus) in a reference system used for navigating the medical procedure (which is also termed a navigation reference system). Image registration is the process of transforming different sets of data into one reference system, in particular a coordinate system. The sets of data to be transformed in the present case are in particular position data comprising position information describing the position of the anatomical body part and the medical imaging apparatus. Registration is desirable in order to be able to compare or integrate the data obtained from different measurements of the position of the anatomical body part and of the position of the medical imaging apparatus. In the present case, the anatomical body part can be said to be registered with the medical imaging apparatus in particular if the following is the case: an n-dimensional image (n being an integer) of the anatomical body part (which image is taken by the medical imaging apparatus) is registered when the spatial location (the position) of each point of the actual object (the actual anatomical body part) within a space, for example an operating theatre, is assigned an image data point of the image. Such a registration of the anatomical body part with a medical imaging apparatus may be corrupted in case the anatomical body part is moved and then has to be updated, in particular corrected, i.e. updated on the basis of the changed relative position between the anatomical body part and the medical imaging apparatus. The inventive method preferably comprises the following steps.

Preferably, initial body part position data is acquired which comprises initial body part position information. The initial body part position information describes in particular an initial relative position between the medical imaging apparatus and the anatomical body part. The initial relative position is in particular the position in which the anatomical body part and the medical imaging apparatus are initially (in particular before execution of the medical procedure) registered with each other. Such a registration may be effected by for example a single step of determining the position of the anatomical body part and the medical imaging apparatus by tracking markers which are attached to them. Alternatively or additionally, the initial relative position may be determined based on information about the identity (which can be gathered by visual identification of an image taken by the medical imaging apparatus) and the position (which can be identified from predetermined positional data gathered for example from a computer tomography of the respective patient's body) of the anatomical body part as well as in particular information about the imaging characteristics of the medical imaging apparatus according to the method of determining a transformation for transforming medical image data into a position reference system which is also described herein. In particular in that case, the initial body part position data can be acquired based on user input. For example, a user such as a surgeon or medical technician may use a pointing tool such as a mouse or a pointer (in particular a pointer for operating a touch screen) to manually enter information on a visual output of the image produced by the medical imaging apparatus at the locations in the image at which the anatomical body part is shown. In particular, the user can draw an outline of the anatomical body part and the position of the outlined image features can be determined using the method of determining a transformation for transforming medical image data into a positional reference system. For example, the outlined image features are substituted as the medical image selection information of that method.

Preferably, body part medical image data is acquired in particular from the medical imaging apparatus. The medical imaging apparatus is preferably at least one of digital still camera, a digital video camera and a digital microscope. The medical image apparatus may therefore be for example an imaging apparatus which combines the functionality of all three kinds of digital imaging apparatus in one device. In particular, the medical imaging apparatus images, i.e. acquires an image (in particular a live image) of the anatomical body part which is described by the body part medical image information. The image is in particular a digital still image or a digital video image, i.e. comprises at least one of a digital photograph or moving image information.

Preferably, actual body part position data is acquired based on the body part medical image data. The actual body part position data comprises actual body part position information which describes in particular an actual relative position between the anatomical body part and the medical imaging apparatus. The actual body part position data is acquired advantageously by substituting the body part medical image information as the medical image information to be acquired by the below-mentioned method of determining a transformation for medical image data into a positional reference system. In particular, the actual body part position data is acquired based on determining a position of a selection of the body part medical image information, the selection representing at least part of the anatomical body part and being substituted as the medical image selection data of the below-described method of determining a transformation for transforming medical image data into a positional reference system.

According to one embodiment, the actual body part position information data can be acquired based on user input, in particular user input of a position of the anatomical body part in the body part medical image information. To this end, the user uses in particular a pointing tool such as a mouse or a pointer (in particular a pointer for a touch screen) to enter information describing the position in a visual display of the body part medical image information. The information may be entered as discrete point information or as contour information (i.e. continuous lines which comprise in particular more than two image units such as pixels). The two-dimensional contour information is preferably mapped into a three-dimensional coordinate system in which a model of the anatomical body part is described. In that coordinate system, the two-dimensional contour is represented by a three-dimensional data object. Details concerning the mapping and the model of the anatomical body part are described below with reference to the method of determining a transformation for transforming medical image data into a positional reference system. The selected part of the body part medical image information can therefore be displayed, in particular, projected, in an image of the model and, if the user's perspective onto the model is changed, the selection can be moved according to the change in perspective. Thus, even in the case of a change of perspective, the user is enabled to view the selection as appropriate. In particular, the selection is transformed into a new three-dimensional data object, the positions of which being defined preferably in the same coordinate system as the positions of the model of the anatomical body part.

In particular in the case in which the medical imaging apparatus is navigated, it is determined whether the medical imaging apparatus has been rotated in particular in the navigation reference system (i.e. the reference system which is used for describing the positions of navigation, for example a global reference system such as a patient-centered reference system) since the point in time at which the initial relative position was acquired or determined, respectively. The three-dimensional data object generated from the initial body part position data is then preferably rotated correspondingly so that its counterpart can be found in the body part medical image data in particular by automatic image feature analysis (such as by running the aforementioned segmentation algorithm). This method feature may also be applied in the case in which image registration is restored by movement of the medical imaging apparatus. However, in that case, it may be applicable to also take into account the rotations of the medical imaging apparatus which are due to the registration restoring movement itself.

According to another embodiment, the actual body part position information data can be acquired automatically, for example by automatic analysis of images. Such an automatic analysis can be implemented in particular by an image segmentation algorithm which is configured to extract specific image features such as contours. Preferably, the user is offered a visual display of different segmented image features so that he can select the applicable segmented image feature which he then can (manually) substitute as the selection from the body part medical image information.

Preferably, body part position transformation data is determined based on the actual body part position data and the initial body part position data. The body part position transformation data comprises body part position transformation information which describes in particular a transformation (more particularly, a positional transformation) between the initial relative position and the actual relative position. The body part position transformation data is in particular determined by comparing the position of the anatomical body part as it is described by the actual body part position information (namely the actual relative position) and/or the position of the anatomical body part in a global (in particular patient-centered) reference system which is determined based on the actual relative position to the initial relative position of the anatomical body part to the position of the anatomical body part in a global (in particular patient-centered) reference system which is determined based on the initial relative position. For example, a shift between an image contour representing the anatomical body part in the actual relative position and an image contour representing the anatomical body part in the initial relative position can be determined. The transformation is then determined preferably based on that shift. The image contours can be generated as described above with regard to generation of the initial body part position and the actual body part position data and, according to a specific embodiment, even a mixture of such methods can be used for determining the transformation. For example, the initial body part position data can be entered manually by using a pointer tool and drawing a contour for example on a touch screen. The actual body part position data can then be determined by segmenting the body part medical image data and searching for image features describing the contour which is used as a basis for determining the initial body part position information. The shift can then be determined automatically. Alternatively, a manually or automatically determined contour describing the anatomical body part in the actual relative position may be manually shifted by a user in a graphical display until an optimal overlap between that contour and an image contour describing the anatomical body part in the initial relative position is reached. The shift between the two contours can then be determined based on the movement of all image features which is necessary to achieve such an overlap.

The positional transformation in particular is a coordinate transformation for transforming the position of the medical imaging apparatus into a reference system in which the position of the anatomical body part is defined or vice-versa (i.e. for transforming the position of the anatomical body part into a reference system in which the position of the medical imaging apparatus is defined). In particular, the aforementioned positions are transformed by applying the transformation. The coordinate transformation in particular takes the form of a linear function which is represented by a transformation matrix, in particular a 4×4 matrix, more particular an affine transformation. If in particular in case the positions of the medical imaging apparatus and the anatomical body part are already defined in the same reference system before applying the transformation, the transformation may take the special form of a mapping which is represented by a vector, i.e. by a 1×0 or 0×1 matrix (depending on the direction of mapping). The body part position transformation information is then preferably used as a basis for adapting the navigation to a positional change which the anatomical body part has undergone in particular relative to the medical imaging apparatus so that the position of the anatomical body part can still be determined on the basis of (in particular from) body part medical image information which is acquired after such a positional change of the anatomical body part. In particular, the initial relative position data may be updated based on the body part transformation data, wherein the updating comprises in particular applying the positional transformation to the initial body part position information. Thereby, the updated initial body part position information may serve as a basis for proceeding with navigation after a change of the relative position in particular between the medical imaging apparatus and the anatomical body part. In particular, the position transformation can serve as a basis for correcting registration of the anatomical body part and the medical imaging apparatus after the relative position between the medical imaging apparatus and the anatomical body part has changed compared to the initial relative position. To this end, preferably three-dimensional navigation data is acquired which comprises three-dimensional navigation information for navigating a medical procedure on the anatomical body part. This three-dimensional navigation data is then preferably updated based on the body part position transformation data, in particular based on the (positional) transformation.

Updating the initial body part position information based on the body part position transformation information includes in particular re-calculating the initial body part position information by applying the (positional) transformation and outputting a visual display of the updated initial body part position information on a display device of a navigation system. To this end, it is not necessary to move the anatomical body part and/or the medical imaging device in particular as long as the anatomical body part is within the viewing field of the medical imaging device. Rather, it in particular suffices to update the graphic (visual) output of the updated information. Thereby, the visual impression of the image of the anatomical body part is updated based on the change to the positional information describing its position.

As mentioned above, the inventive method serves update, in particular correction, of the registration of the medical imaging apparatus with the anatomical body part. In particular, the position of the medical imaging apparatus in a coordinate system in which the position of the anatomical body part is defined is updated. The inventive method seeks to conduct such an update by updating the information about the relative position between the medical imaging apparatus and the anatomical body part. This updated information is preferably acquired by updating the initial body part position information based on the body part position transformation information as described above. For example, a registration matrix which stores information about the spatial relationship between the entities to be registered is updated based on the body part position transformation information.

The body part position transformation data preferably serves as a basis for adjusting the relative position between the anatomical body part and the medical imaging apparatus so that the anatomical body part can be (in particular continuously) imaged by the medical imaging apparatus (in particular so that the actual relative position becomes equal to the initial relative position). In particular, the medical imaging apparatus may be moved based on at least one of user interaction (for example, by manual movement or the medical imaging apparatus) and movement control data comprising movement control information. Such movement control data is preferably determined based on the body part position transformation data and the movement control information describes in particular a command issued to a moving unit for moving the medical imaging apparatus relative to the anatomical body part. The moving unit is advantageously operatively coupled to the medical imaging apparatus and at least the computer of the navigation system used for navigating the respective medical procedure. The navigation system, in particular its computer, then issues the command for moving the medical imaging apparatus to the moving unit. The moving unit may for example take the form of an electric motor or hydraulically actuated cylinders. These features support the ability to image the anatomical body part even after the relative position between the medical imaging apparatus and the anatomical body part has changed compared to the initial relative position. In the case of moving the medical imaging apparatus based on user interaction, preferably a visual indicating device such as a monitor outputs in particular information to the user based on the body part position transformation data for informing the user how to move the medical imaging apparatus in particular to restore the initial relative position or at least a relative position between the anatomical body part and the medical imaging apparatus in which the medical imaging apparatus is able to image the anatomical body part. For example, at least one of the initial body part position information and the actual body part position information can be highlighted in a visual display of the body part medical image information such as on a monitor of a navigation system used for conducting the navigated medical procedure. The user can then deduce from a visual comparison of the displayed image information how to move the medical imaging apparatus relative to the anatomical body part in order to attain an imaging position, i.e. positioning in which medical imaging apparatus is able to image the anatomical body part. This feature may also be used in connection with the embodiment in which the medical imaging apparatus is moved by a moving unit since it also supports visual verification of a correct functioning of the moving unit. In particular, the user and/or the moving unit will strive to achieve an overlay of the highlighted initial body part position information and actual body part position information in the display in order to restore the initially acquired registration of the anatomical body part and medical imaging apparatus.

Preferably, it is monitored during execution of the inventive method whether the actual relative position differs from the initial relative position and, if this is the case, the step of determining the body part position transformation data is executed. Further preferably, a visual and/or audio warning (e.g. a graphical feature projected into the body part medical image information) is issued to the user if such a difference is determined. Such a monitoring can be implemented for example by continuous segmentation of the body part medical image information in order to find a representation of the anatomical body part and then determining the position of the anatomical body part based on that representation. The position of the anatomical body part is determined advantageously by applying the method of determining a transformation for transforming medical image data into a positional reference system which is described below. In particular, the initial body part position data comprises information about a spatial feature of the anatomical body part such as its size (in particular, volume or characteristic geometry quantity such as diameter) and/or shape (which is represented preferably by a contour of the anatomical body part). On that basis, the body part medical image information is analyzed for corresponding image features.

The disclosed method, in particular any method step associated with or directed to acquiring the initial body part position data, the body part medical image data or the actual body part position data, does not involve an invasive step which would represent the substantial physical interference with the human or animal body requiring professional medical expertise to be carried out and entailing a substantial health risk even when carried out with the required professional care and expertise. Furthermore, no part of the inventive method involves a step of treating a human or animal body using surgery or therapy. Rather, the invention is said to also relate to a method of operating, in particular controlling, a medical navigation system which involves determining the position of an anatomical structure represented by a selection from the medical image information.

The present invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The present invention also relates to a navigation system for a medical procedure, in particular an image-guided medical procedure. The navigation comprises preferably at least the aforementioned computer for processing data, in particular acquiring and determining data; a detection device for detecting the position of the medical imaging apparatus; and a data interface for receiving information about the position of the medical imaging apparatus for supplying that information to the computer.

* * *

The present invention preferably also makes use of (in particular, incorporates the features of) a method, in particular a data processing method, of determining a transformation for transforming medical image data into a positional reference system. That method is described in the applicant's co-pending PCT application having the title "Three-dimensional image segmentation based on two-dimensional image information" and the attorney's reference 58 860 VI which was filed on the same day as this application. That method is preferably executed by a computer and preferably comprises the following steps and/or features which are part of the present invention and is also considered to form part of the present disclosure. An account of that method is given in the following.

Preferably, medical image data is acquired from a medical imaging apparatus. The medical image data comprises medical image information which describes in particular a two-dimensional image of an anatomical body part. The medical imaging apparatus is at least one of a video camera, a microscope or a camera for taking still images. The medical imaging apparatus can also be embodied by an endoscope which in particular comprises at least one of the aforementioned types of imaging apparatus. Besides that, the medical imaging apparatus may also be embodied by a magnetic resonance or computer tomography or conventional X-ray apparatus. In case the medical imaging apparatus is a video camera, the medical image information preferably is video information which is in particular taken in-situ, i.e. video information which comprises image information describing a surgical situs. If the medical image apparatus is embodied by a microscope or a still image camera, the medical image information is in particular still image information, in particular in-situ still image information, i.e. still image information describing a surgical situs. The medical image information is preferably defined in two dimensions and therefore represents a two-dimensional image of a three-dimensional structure, in particular of an anatomical body part. The anatomical body part in particular comprises at least one of soft tissue (for example, brain tissue, liver tissue, or lung tissue) and bony tissue (for example, bone or cartilage).

Preferably, the medical imaging apparatus is navigated. For example, medical imaging apparatus position data is acquired which comprises medical imaging apparatus position information. For example, at least one marker for detection by a navigation system is attached to the medical imaging apparatus with a predetermined and preferably fixed spatial relationship relative to the medical imaging apparatus.

Preferably, also the anatomical body part is navigated. For example, anatomical body part position data is acquired which comprises anatomical body part position information. For example, at least one marker for detection by a navigation system is attached to the body of the patient to whom the anatomical body part belongs. The at least one marker is attached to the body in particular with a predetermined and preferably also fixed spatial relationship relative to the anatomical body part. The spatial relationship is preferably known within the framework of the inventive method. For example, medical image data such as image data acquired from a CT scanner which represents the anatomical body part may be acquired before or during execution of the inventive method and serve as a basis for determining that spatial relationship between the at least one marker and the anatomical body part. Thereby, the position of the anatomical body part may be tracked by the navigation system during execution of the inventive method.

It is the function of a marker to be detected by a marker detection device (for example, a camera or an ultrasound receiver or analytical devices, like CT or MRI), such that its spatial position (i.e. its spatial location and/or alignment)

can be determined. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or one marker or more than one (individual) markers which are preferably in a predetermined spatial relationship. A marker device comprises one, two, three or more markers which are in case of two or more markers in a predetermined spatial relationship. This predetermined spatial relationship is in particular known to a navigation system and for example stored in a computer of the navigation system.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU), a working memory, advantageously an indicating device for issuing an indication signal (for example, a visual indicating device such as a monitor and/or an audio indicating device such as a loudspeaker and/or a tactile indicating device such as a vibrator) and advantageously a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

The medical imaging apparatus position information describes in particular a position of the medical imaging apparatus in a navigation coordinate system. The navigation coordinate system is in particular a coordinate system in which positions of interest, in particular the positions of medical instruments, the medical imaging apparatus and the anatomical body part are defined during a medical procedure and in which the navigation data processed by the navigation system describes it.

Preferably, medical image selection data is acquired by the inventive method which comprises medical image selection information. The medical image selection information describes (in particular, represents and/or is) in particular a selection from the medical image information, i.e. a subset of the medical image information. The medical image selection data, in particular the medical image selection information, is acquired preferably based on user inputs, in particular determined by marking image features which are displayed to the user based on for example touch-screen input or pointer to input. By doing so, the user is enabled to mark at least one specific region of the anatomical body part which is of particular interest to him. Preferably, the medical image selection information comprises metadata comprising metainformation describing the selection such as contour information describing a contour in the medical image information. The contour may for example be highlighted for visual recognition by the user and preferably delineates a region of interest which belongs to the anatomical body part. Alternatively or additionally, the medical image selection information may comprise point image information, in particular consist of a single image information unit such as a pixel. The medical image selection data may alternatively or additionally be determined automatically, for example by segmentation of the medical image information to detect image features such as contours and preferably outline them automatically. In particular, an image segmentation algorithm is run on the medical image information in order to determine such image features. Advantageously, the inventive method provides a user with a possibility of interaction and re-running the image segmentation algorithm (preferably with different parameters than before) in case the image segmentation algorithm in the first place leads to wrong detection of the image features (which may be checked for example by user interaction, in particular by viewing the output). In the case of automatic determination of the medical image selection data, the user is preferably presented with the result of such an automatic determination in particular in the form of a graphical display of the image features. In most cases, the automatic determination will lead to detection of numerous in particular coherent image features, in particular of image regions. The user is therefore preferably provided with a possibility of interaction for manual selection of the desired image feature (image region) as the selection from the medical image data.

Preferably, imaging apparatus characteristic data is acquired which comprises imaging apparatus characteristic information. The imaging apparatus characteristic information describes in particular an imaging characteristic of the medical imaging apparatus. The imaging characteristic in particular is an optical quantity which describes the optical properties of the medical imaging apparatus. More particularly, the imaging characteristic is the position of the focal plane, in particular the focal length, of the medical imaging apparatus. Preferably, the imaging apparatus characteristic data also comprises information about the geometry of the medical imaging apparatus, in particular information about the position of an image generating part of the medical imaging apparatus such as a lens (in particular in the case of the medical imaging apparatus being a video camera, microscope or still image camera) or of the corresponding imaging characteristics of an X-ray-based medical imaging apparatus such as a CT or X-ray apparatus. These corresponding imaging characteristics are preferably described by focal length correspondence information contained in focal length correspondence data which is preferably acquired by the inventive method. The corresponding characteristics of such apparatuses comprise for example information about the energy and/or wavelength of the used X-rays, information about the image contrast in particular at image contours or information about light intensity patterns at at least two spaced-apart locations in the medical image information (for phase detection). Alternatively or additionally, the focal length correspondence information may describe the image entropy of the medical image information which may be used as a physical quantity (in particular for a medical image taken with an X-ray-based medical imaging apparatus) which corresponds to the focal length of a lens-based classical imaging apparatus such as a video camera, microscope or still image camera. In a grey scale image, the image entropy is understood to be a statistical measure of randomness that can be used to characterize the texture of the grey scale image. For example, an image consisting of only black or only white colour information has no image entropy, while more complex images having both black and white colour values and/or a grey scale colour values lying inbetween black and white have a positive value of image entropy. It is generally assumed that, the lower the value of image entropy is, the more focussed the (in particular X-ray-based) image appears, in particular the clearer contours are rendered in the image.

Alternatively or additionally, the focal length correspondence information for an X-ray-based medical imaging apparatus may describe the focal length of refractive-X-ray optics used for focussing the X-rays.

Preferably, the medical image information is focussed image information. In particular, the medical image information describes a physical structure, more particularly the anatomical body part, which was imaged by the medical imaging apparatus at a distance from the medical imaging apparatus which corresponds to (in particular is equal to) its focal length. Thereby, the distance between the imaged physical structure and in particular the image generating unit can be determined based on the imaging apparatus characteristic information and in particular the focal length correspondence information Preferably, selection position data is determined based on the medical image data (in particular, the medical image information), the medical image selection data (in particular, the medical image selection information) and the imaging apparatus characteristic data (in particular, the imaging apparatus characteristic information). The selection position data preferably comprises a selection position information which describes in particular a three-dimensional position of a physical (in particular, anatomical) structure (which belongs in particular to the anatomical body part and can comprise at least one of soft tissue and bony tissue). The anatomical structure corresponds to the selection from the medical image information. In particular, the selection position information describes the three-dimensional position of the physical structure in the navigation reference system. The selection position information therefore is determined preferably additionally based on the medical imaging apparatus position data. Preferably, the selection position data is determined by mapping the medical image selection data onto a model of the anatomical body part. The medical image selection data, in particular the selection from the medical image information, is preferably defined in two dimensions, and the model of the anatomical body part is preferably defined in three dimensions. The model of the anatomical body part is advantageously determined and preferably generated based on medical image data acquired from a computer tomography or magnetic resonance tomography, in particular by segmenting CT-based or MRT-based medical image information which describes, in particular represents the anatomical body part. The two-dimensional medical image selection information is then mapped onto such a pre-segmented three-dimensional model of the anatomical body part in particular based on a transformation which transforms the two-dimensional medical image selection information into the three-dimensional coordinate system in which the model of the anatomical body part is defined. The transformation is preferably determined during execution of the inventive method. It is determined in particular based on information about the position of the medical imaging apparatus relative to the anatomical body part which is advantageously acquired based on the position information acquired by navigation of at least one of the medical imaging apparatus and the anatomical body part. The transformation is determined preferably further based on the imaging apparatus characteristic information. Thereby, a positional relationship between the image features described by the medical image information and the anatomical body part can be determined. Such mapping of the selection position information onto the model of the anatomical body part is in particular useful for providing a visual display of the selection (i.e. the anatomical structure) in a model of the anatomical body part which is used in particular as visual guidance information for conducting a navigated medical procedure. The mapping into the three-dimensional coordinate system in which the anatomical body part is described provides the advantage of being able to move, in particular shift and/or rotate, the visual display of the model of the anatomical body part while enabling to have image data describing (in particular representing) the selection still displayed in the model in the corresponding perspective. Therefore it is an aim of the inventive method to provide a graphical display of the selection from the medical image data as a mapping of the selection onto a three-dimensional model of the anatomical body part while assuring that the selection is displayed in the correct perspective, in particular in the perspective from which the model is viewed in particular by a user.

Assuming that the medical image information is focussed image information, the selection position data is determined preferably based on focal transformation data comprising focal transformation information. The focal transformation information describes in particular a transformation (more particularly, a mapping) from the imaging plane of the medical imaging apparatus to the focus of the medical imaging apparatus. The focal transformation information more particularly describes rotations and translations between the focus of the medical imaging apparatus and the imaging position to which a point lying in that focus is projected during the imaging process. The imaging position is in particular located in an imaging plane of the medical imaging apparatus such as in particular the surface of a semiconductor-based imaging element. The rotations and translations are embodied in particular by an affine (linear) transformation which is described preferably by 4×4 matrices or a single-column vector (depending on the number of degrees of freedom to be transformed, in particular mapped).

Preferably, three-dimensional navigation data comprising three-dimensional navigation information for navigating a medical procedure on the anatomical body part is acquired. The three-dimensional navigation information is used in particular for informing the user about a position of a medical instrument in particular relative to the anatomical body part. The medical instrument may be for example a cauter or a cutting instrument. Preferably, the three-dimensional navigation information is updated based on the selection position data (in particular, based on the selection position information). Thereby, the user is provided with updated information about the position of the selected anatomical structure for example in case a change in the anatomical structure has taken place (for example, due to surgical removal of tissue which in particular in the case of soft tissue may lead to a positional change of the remaining tissue).

Preferably, the medical image information is overlaid with functional image information which describes in particular a function (more particularly a physiologic function) of the anatomical body part. Such an overlay with functional image information may be used to highlight anatomical regions of interest to the user which may be in particular organs at risk, affection of which by the medical procedure should be avoided. Thereby, the user is supported in navigating the medical procedure and also given additional information on the basis of which he may enter his user input for acquiring the medical image selection data. Such an overlay is preferably effected based on the selection position information and in particular also predetermined medical image information (which has been in particular generated by a CT scanner) describing the anatomical body part. On that basis, it can be determined which anatomical region of a patient's body is currently being imaged by the medical imaging device and corresponding predetermined medical image information can be determined in particular based on the selection position information. The corresponding medical image information is preferably associated with the functional image information.

Preferably, navigation of the medical procedure comprises a visual output to the user which informs him about the visual appearance of the surgical situs. The visual output in particular takes the form of a three-dimensional model of the anatomical body part. Preferably, the selection from the medical image information is displayed in this visual output based on the selection position data so that the user is given an impression of (in particular, visual information about) the position of the selection relative to the rest of the anatomical body part.

The disclosed method, in particular any method step associated with or directed to acquiring the medical image information or the medical image selection information, does not involve an invasive step which would represent the substantial physical interference with the human or animal body requiring professional medical expertise to be carried out and entailing a substantial health risk even when carried out with the required professional care and expertise. Furthermore, no part of the inventive method involves a step of treating a human or animal body using surgery or therapy. Rather, the method is said to also relate to a method of operating, in particular controlling, a medical navigation system which involves determining the position of an anatomical structure represented by a selection from the medical image information.

In the following, a short general account of the aforementioned method is given.

The method is in particular directed to offering a user such as a surgeon or a medical technician an easy and intuitive way of segmenting structures of interest in a two-dimensional video image and making those structures available in a three-dimensional model of the anatomical body part. The user simply outlines the structures in the two-dimensional medical image information and the two-dimensional outline is calculated back onto the three-dimensional image model data by means of the navigation system. For example, a two-dimensional segmented object such as a craniotomy may be used in combination with a three-dimensional segmented skull and a skull may then be clipped to represent the craniotomy in the three-dimensional model.

Another application of that method includes outlining vessel structures on the cortex as visualized by a contrast agent (in particular indocyanine green—ICG) microscopy. Such contrast agent microscopy can be used to visualize arterial and veinial vessels through the dura after opening the skull. Veins marked by the contrast agent ("glowing" veins) can be easily outlined on the two-dimensional video image (manually or automatically) and in combination with the segmented three-dimensional cortex in the navigation model, a three-dimensional representation of the vessel on the cortex can be determined. The vessel objects are then available before further navigation persistently even if the application of the contrast agent ceases.

Embodiments of the method described in the co-pending application are the following:

A. A data processing method of determining a transformation for transforming medical image data into a positional reference system, the method being executed by a computer and comprising the following steps:
  a) acquiring, from a medical imaging apparatus, medical image data comprising medical image information describing a two-dimensional image of an anatomical body part;
  b) acquiring medical image selection data comprising medical image selection information describing a selection from the medical image information;
  c) acquiring imaging apparatus characteristic data comprising imaging apparatus characteristic information describing an imaging characteristic of the medical imaging apparatus;
  d) determining, based on the medical image data, medical image selection data and imaging apparatus characteristic data, selection position data comprising selection position information describing a three-dimensional position of an anatomical structure in the anatomical body part, the anatomical structure corresponding to the selection from the medical image information.

B. The method according to the preceding embodiment, wherein the selection from the medical image information is represented by two-dimensional image information and is mapped onto a three-dimensional model of the anatomical body part.

C. The method according to any one of the preceding embodiments, wherein the medical imaging apparatus characteristic information comprises optical characteristic information describing an optical characteristic of the medical imaging apparatus.

D. The method according to the preceding embodiment, wherein the optical characteristic is the focal length position of the focal plane of the medical imaging apparatus.

E. The method according to any one of the preceding embodiment, wherein the medical image information is focussed image information.

F. The method according to any one of the preceding embodiments, wherein the medical image information is video information, in particular in-situ video information, and the medical imaging apparatus is a video camera or wherein the medical image information is still image information and wherein the medical image apparatus is a microscope or a camera for taking still images.

G. The method according to any one of the preceding embodiments, wherein the selection position data is determined based on focal transformation data comprising focal transformation information describing a transformation from the imaging plane of the medical imaging apparatus to the focus of the medical imaging apparatus.

H. The method according to any one of the preceding embodiments, wherein three-dimensional navigation data comprising three-dimensional navigation information for navigating a medical procedure on the anatomical body part is acquired and wherein the three-dimensional navigation information is updated based on the selection position data.

I. The method according to any one of the preceding embodiments, wherein medical imaging apparatus position data is acquired comprising medical imaging apparatus position information describing a position of the medical imaging apparatus in a navigation coordinate system and wherein the medical image selection data is determined based on the medical imaging apparatus position data.

J. The method according to any one of the preceding embodiments, wherein the medical image information is overlaid with functional image information describing a function of the anatomical body part.

K. The method according to any one of the preceding embodiments, comprising a step of displaying the selection from the medical image information based on the selection position data.

L. The method according to the preceding embodiment, wherein the selection from the medical image information is overlaid on visual guidance information used for conducting a navigated medical procedure.

M. The method according to any one of the preceding claims, wherein the medical image selection data is acquired based on at least one of user input, in particular touch-screen or pointer tool input, and automatic determination of image features described by the medical image information, in particular by running an image segmentation algorithm on the medical image information.

N. A program which, when running on a computer or when loaded onto a computer, causes the computer to perform the method steps according to any one of the preceding embodiments and/or a program storage medium on which the program is stored in particular in a non-transitory form and/or a computer, in particular a cloud computer, on which the program is running or into the memory of which the program is loaded and/or a signal wave, in particular a digital signal wave, carrying information which represents the program, in particular the aforementioned program, which in particular comprises code means which are adapted to perform the method steps according to one of the preceding embodiments.

O. A navigation system for a medical procedure, in particular an image-guided medical procedure, comprising:
  the computer of the preceding embodiment, for processing the medical image data, medical image selection data and imaging apparatus characteristic data;
  a detection device for detecting the position of the medical imaging apparatus;
  a data interface for receiving information about the position of the medical imaging apparatus for supplying that information to the computer.

The methods described in the present disclosure in particular are data processing methods. The data processing methods are preferably performed using technical means, in particular a computer. The data processing methods are in particular executed by or on the computer.

Preferably, the inventive method is at least partly executed by a computer. That is, all steps or just some of the steps (i.e. less than a total number of steps) of the inventive method may be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

Within the framework of this disclosure, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information". Where in the framework of this disclosure it is said that information describes an entity, the respective information in particular represents that entity. Where it is said that data processing is carried out on "XY data", it is to be understood that this data processing is carried out in particular on the corresponding "XY information".

In the following, a specific embodiment of the invention shall be described with reference to the figures. The specific embodiment shall not be understood to limit the invention only to those features shown in the figures.

Figure 1A:
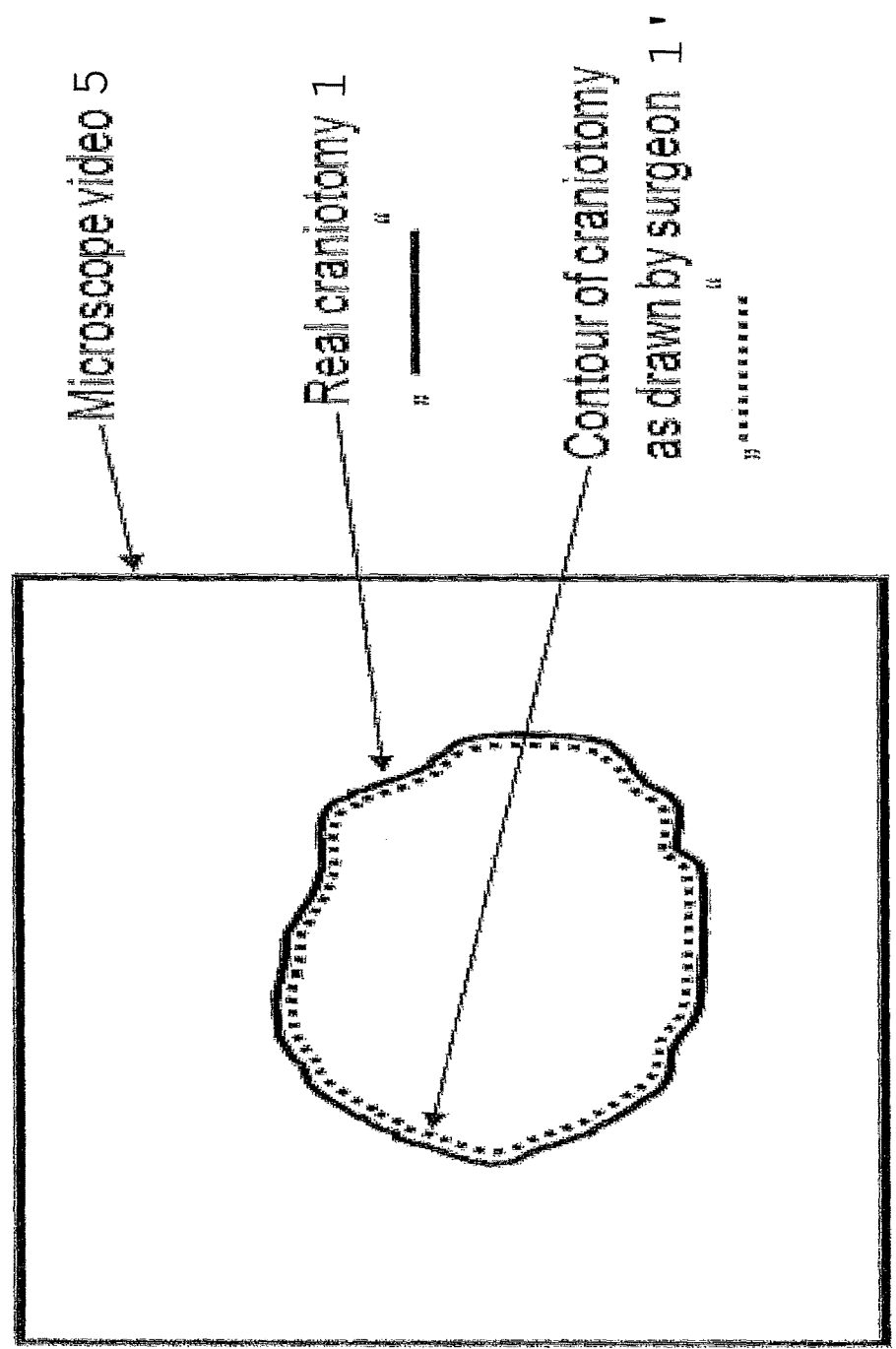
FIGS. 1a and 1b show a way of generating the initial body part position data by manual input.
Figure 1B:
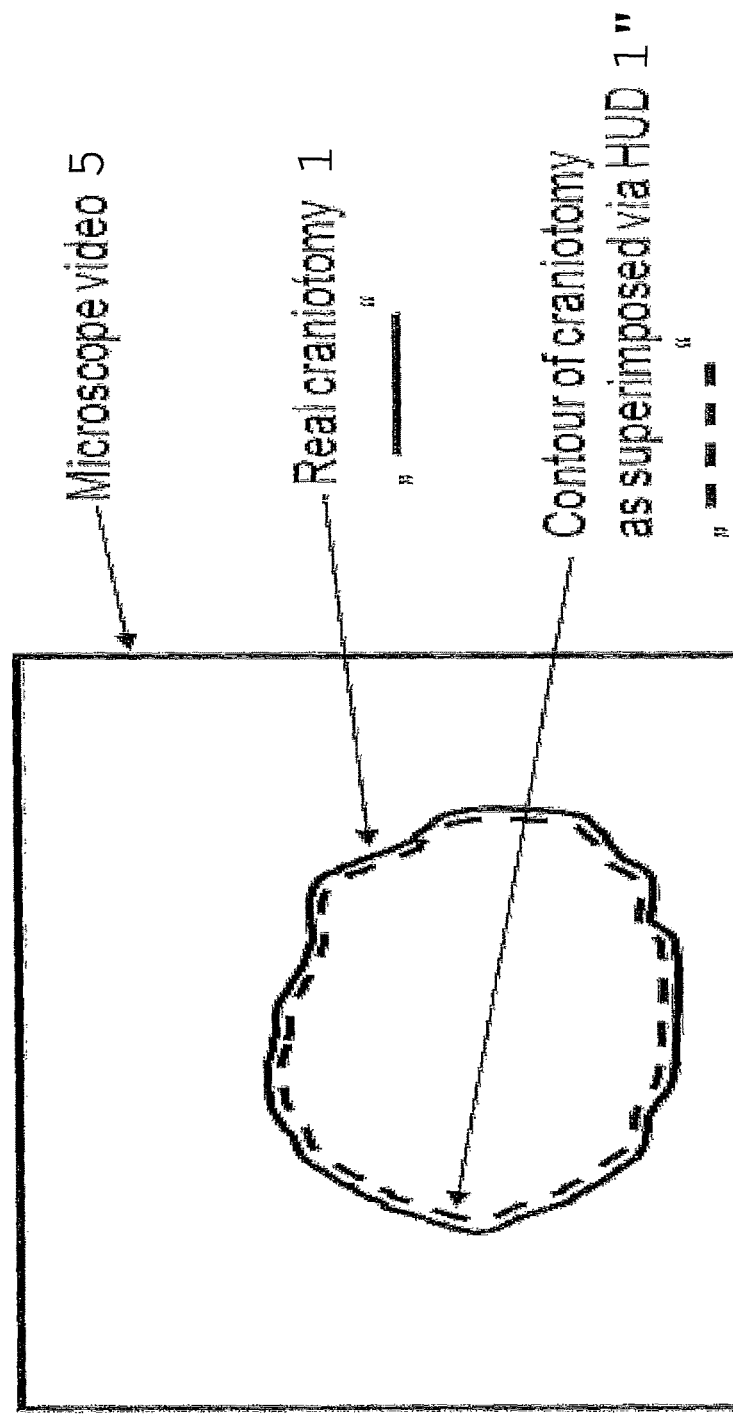

According to FIG. 1a, a user, for example a surgeon, manually draws a contour line 2 representing the initial body part position information in the display of a microscope video 5 representing the body part medical image information. The contour line 1' represents the contour of a real craniotomy 1 as the anatomical body part. As shown in FIG. 1b, the contour line 1' is transformed into a three-dimensional virtual data object 1" which is superimposed onto the graphical display of the real craniotomy 1 as imaged in the microscope video 5.

Figure 2:
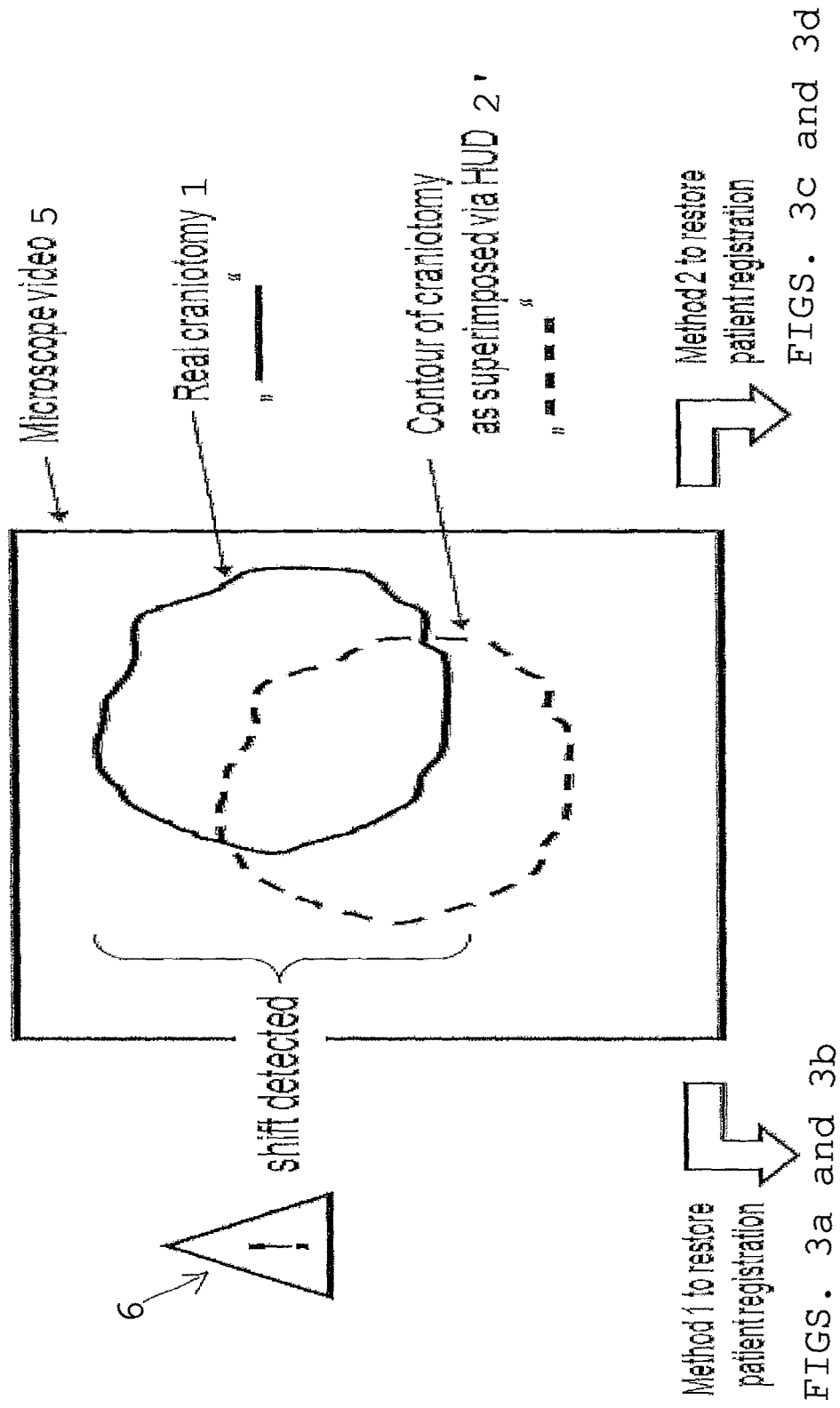
FIG. 2 shows a way of detecting a shift between the initial relative position and the actual relative position and issuing a corresponding warning.

FIG. 2 shows how a shift between the actual relative position of the real craniotomy 1 and the initial relative position of the craniotomy represented by the three-dimensional object 1" is detected. In this example, the shift is detected based on a difference in the display locations of the respective image features. A corresponding warning 6 is issued to inform a user about detection of such a shift. The warning 6 comprises a graphical symbol and a text message "shift detected". Based on the detection of a shift, two different methods of restoring patient registration relative to the medical imaging apparatus (in this case a microscope comprising a video camera) are executed.

Figure 3A:
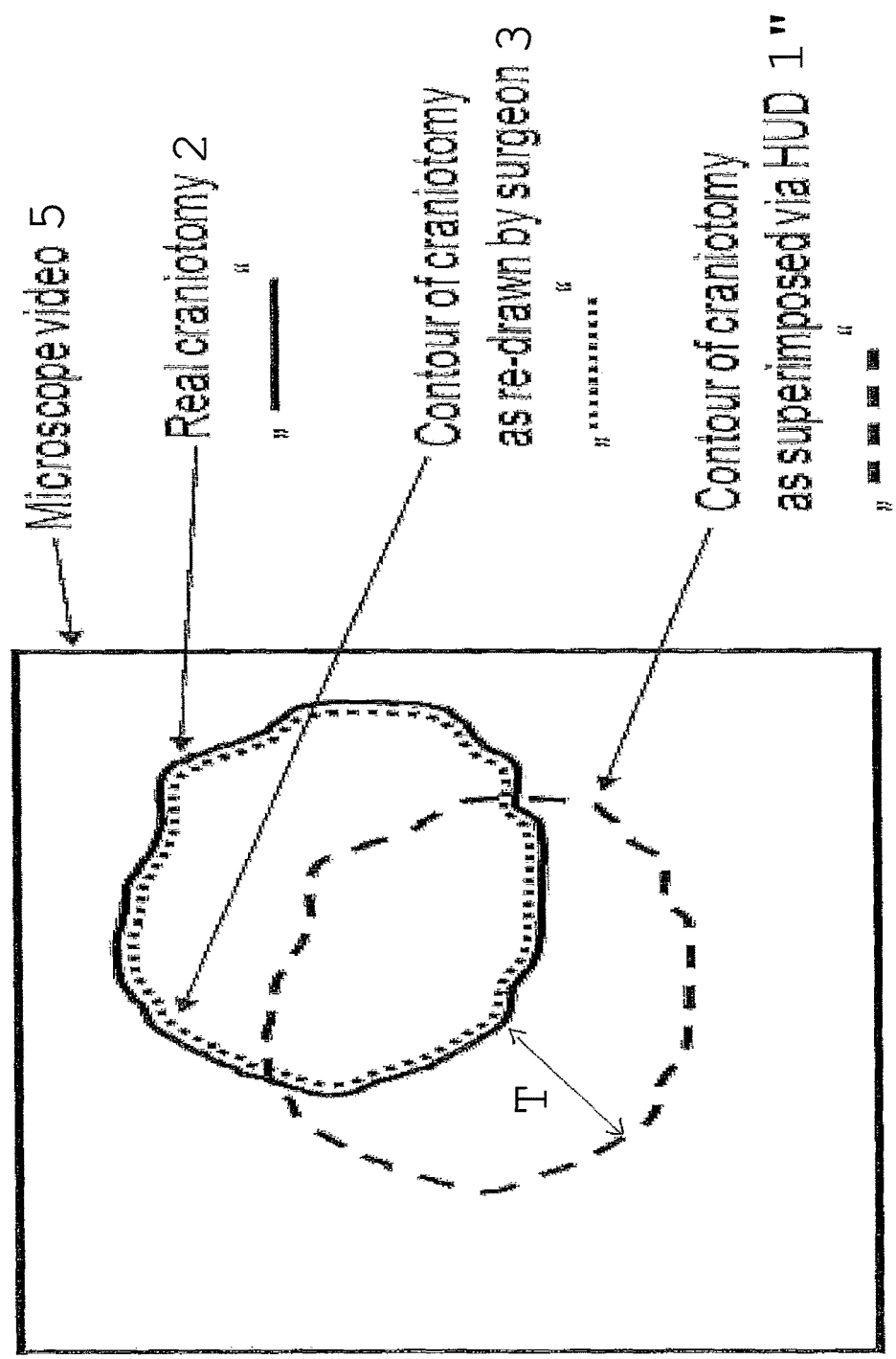
FIGS. 3a and 3b show a first method of determining the body part position transformation information.
Figure 3B:
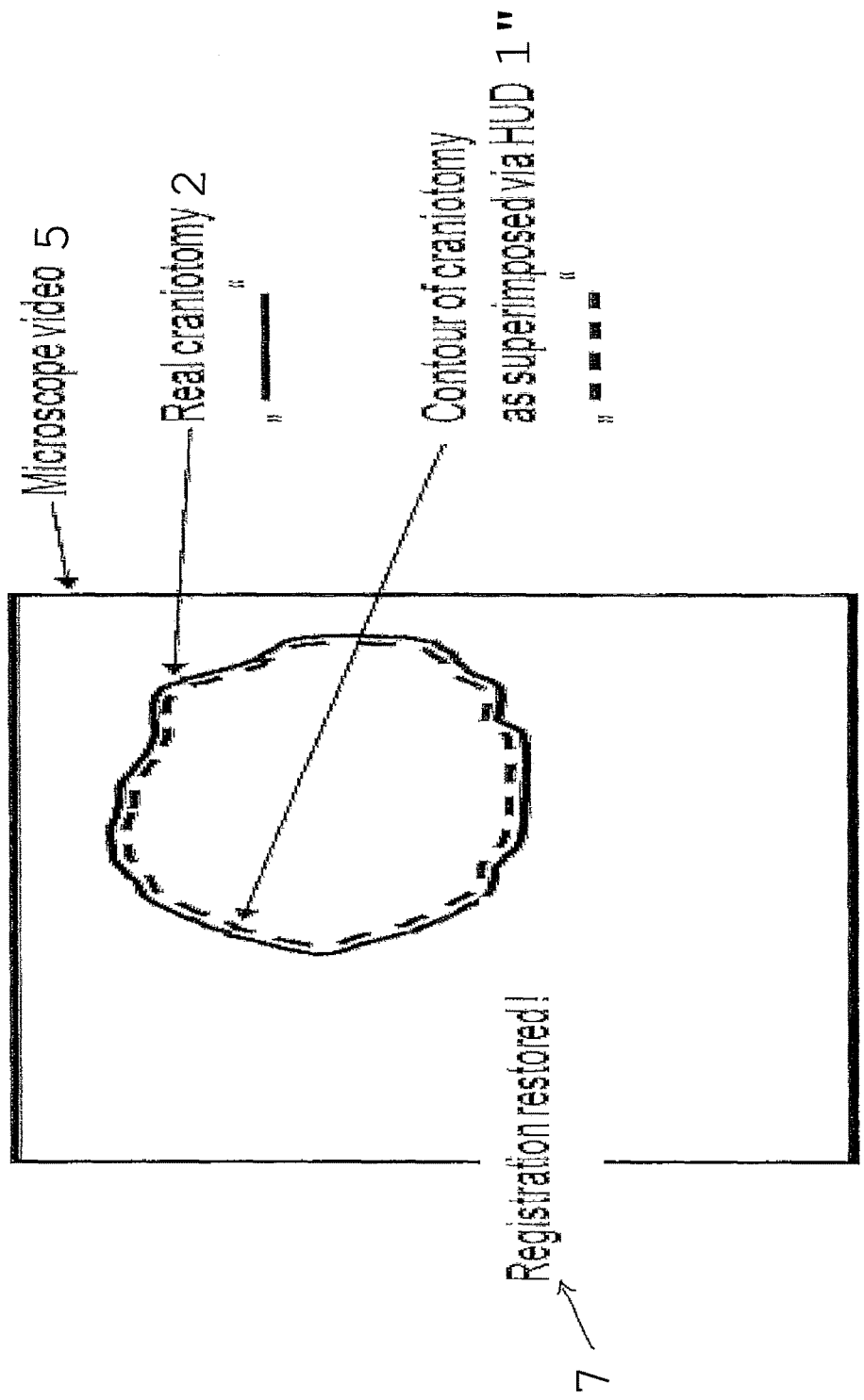

The first method is described by FIGS. 3a and 3b. According to FIG. 3a, the user, for example a surgeon, draws a contour 3 of the real craniotomy 2 (which in this case represents the anatomical body part in the actual relative position and therefore has been assigned a reference sign different from that used in FIGS. 1a and 1b). A transformation T representing the body part transformation information is determined between the image features representing the contour 3 and the contour 1". According to FIG. 3b, the three-dimensional object represented by the contour line 1" is then shifted by subjecting it to the transformation T so that the contour line 1" is superimposed in the image supplied by the microscope video 5 onto the image features describing the real craniotomy 2. Thereby, information about the relative position between the medical imaging apparatus (microscope) and the anatomical body part (real craniotomy) is updated. The user may then receive a graphical output such as a text information 7 which in this case reads "Registration restored!".

Figure 3C:
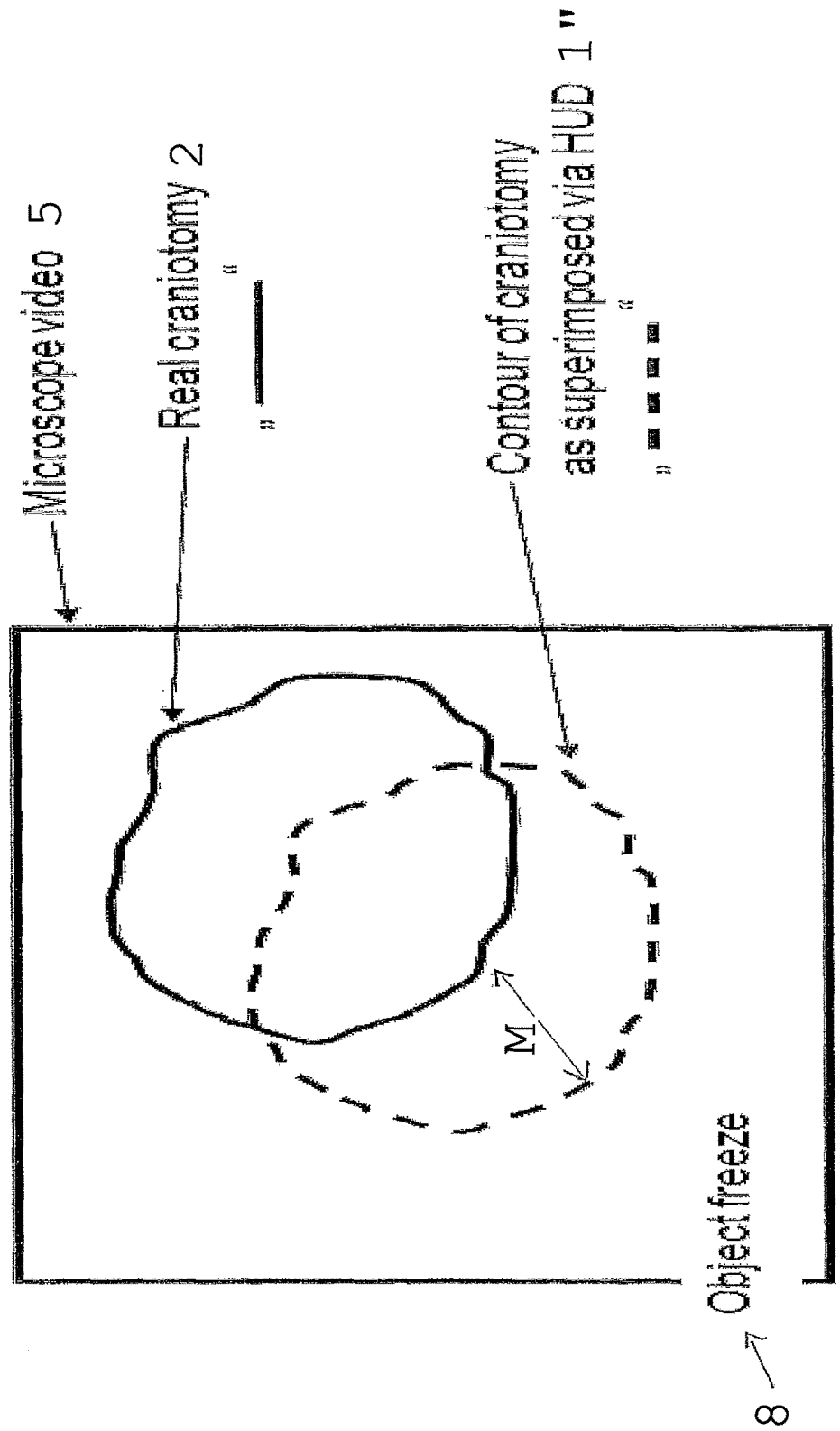
FIGS. 3c and 3d show a second method of determining the body part position transformation information.
Figure 3D:
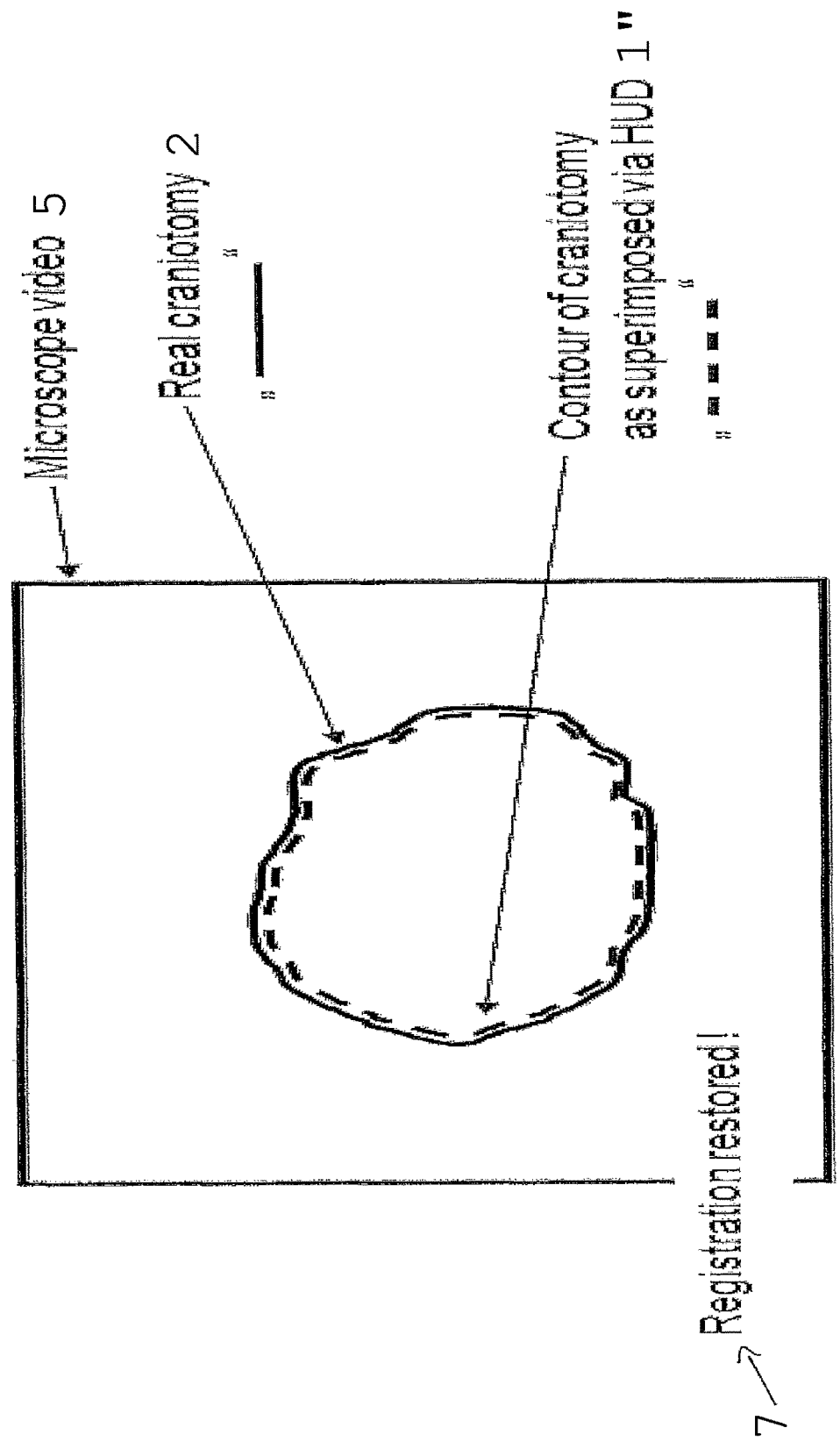

The second method of restoring registration is described by FIGS. 3c and 3d. According to FIG. 3c, the transformation T is restored by moving the medical imaging apparatus (microscope) such that the image of the real craniotomy 2 (representing the anatomical body part in the actual relative position) in a movement direction M. To this end, the image of the microscope video 5 is preferably frozen so that the user is given a steady image so that he can achieve a display state in which the image of the real craniotomy 2 and the contour 1" of the three-dimensional object representing the craniotomy in the initial relative position overlap. In this example, the user is supplied with a text message "object freeze" in order to inform him that a steady image is being output. The movement of the medical imaging apparatus relative to the anatomical body part (real craniotomy 2) is preferably tracked by a navigation system which is used for determining the position of in particular the medical imaging apparatus. Based on tracking of that movement, the body part position transformation information (in particular, the corresponding transformation) is determined which describes that movement M. Based on that transformation, the registration matrix which is used to describe the relative position between the medical imaging apparatus and the anatomical body part where the envisaged medical procedure is updated and, as shown in FIG. 3d, the user may be provided with a text message 7 "Registration restored!".

Therefore, the two different methods described by FIGS. 3a, 3b and 3c, 3d, respectively, are directed to determining the body part position transformation information by image segmentation and virtual movement of the medical imaging apparatus relative to the anatomical body part and to physically moving the medical imaging apparatus back into the initial relative position, respectively.

The invention claimed is:

1. A navigation system for a medical procedure comprising:
   a computer having a non-transitory computer readable medium which stores a program which, when executed by the computer or loaded onto the computer, causes the computer to execute a method of determining a positional transformation for registering an anatomical body part with a medical imaging apparatus, the method comprising the following steps executed by the computer:
   a) acquiring, at the computer, initial body part position data comprising initial body part position information describing an initial relative position between the medical imaging apparatus and the anatomical body part;
   b) acquiring, at the computer and from the medical imaging apparatus, body part medical image data comprising two-dimensional body part medical image information describing an image of the anatomical body part;
   c) acquiring, at the computer and based on determining a position of a selection from the body part medical image information and corresponds to the anatomical body part, wherein the selection represents at least part of the anatomical body part, actual body part position data comprising actual body part position information describing an actual relative position between the anatomical body part and the medical imaging apparatus;
   d) determining, by the computer and based on the actual body part position data and the initial body part position data, body part position transformation data comprising body part position transformation information describing a transformation between the initial relative position and the actual relative position,
   wherein acquiring the actual body part position data comprises determining, by the computer, the actual relative position as a three-dimensional position based on information about the focal length of the medical imaging apparatus; and
   a detection device for detecting the position of the medical imaging apparatus;
   a data interface for receiving information about the position of the medical imaging apparatus for supplying that information to the computer.

2. A method of determining a positional transformation for registering an anatomical body part with a medical imaging apparatus, the method being executed by a computer and comprising:
   a) acquiring, at the computer, initial body part position data comprising initial body part position information describing an initial relative position between the medical imaging apparatus and the anatomical body part;
   b) acquiring, at the computer and from the medical imaging apparatus, body part medical image data comprising two-dimensional body part medical image information describing an image of the anatomical body part;
   c) acquiring, at the computer and based on determining a position of a selection from the body part medical image information, wherein the selection represents at least part of the anatomical body part and corresponds to the anatomical body part, actual body part position data comprising actual body part position information describing an actual relative position between the anatomical body part and the medical imaging apparatus;
   d) determining, by the computer and based on the actual body part position data and the initial body part position data, body part position transformation data comprising body part position transformation information describing a transformation between the initial relative position and the actual relative position,
   wherein acquiring the actual body part position data comprises determining, by the computer, the actual relative position as a three-dimensional position based on information about the focal length of the medical imaging apparatus.

3. The method according to claim 2, further including adjusting, based on the body part position transformation data, the relative position between the anatomical body part and the medical imaging apparatus so that the anatomical body part can be imaged by the medical imaging apparatus.

4. The method according to claim 2, wherein adjusting the relative position between the anatomical body part and the medical imaging apparatus comprises at least one of moving the medical imaging apparatus based on user interaction and determining, based on the body part position transformation data, movement control data comprising movement control information to a moving unit operatively coupled the medical imaging apparatus, the movement control information describing a command issued to the moving unit for moving the medical imaging apparatus relative to the anatomical body part.

5. The method according to claim 2, wherein the initial body part position data is acquired based on user input.

6. The method according to claim 2, wherein the actual body part position data is determined based on user input.

7. The method according to claim 2, wherein the initial relative position data is updated based on the body part position transformation data, wherein the updating further includes applying the transformation to the initial body position information.

8. The method according to claim 2, wherein the body part medical imaging information describes at least one of a live image of the anatomical body part.

9. The method according to claim 8, wherein the medical imaging apparatus is at least one of a digital still camera, a digital video camera and a digital microscope.

10. The method according to claim 8, wherein three-dimensional navigation data comprising three-dimensional navigation information for navigating a medical procedure on the anatomical body part is acquired and wherein the three-dimensional navigation data is updated based on the body part position transformation data.

11. The method according to claim 8, wherein at least one of the initial body part position information and actual body part position information is highlighted in a display of the body part medical image information.

12. A non-transitory computer readable program storage medium on which a program is stored which, when running on a computer or when loaded onto a computer, causes the computer to perform the method steps according to claim 2.

\* \* \* \* \*